United States Patent
Geisel

(10) Patent No.: US 6,677,763 B2
(45) Date of Patent: *Jan. 13, 2004

(54) MATERIAL SEGREGATION, DENSITY, AND MOISTURE ANALYZING APPARATUS AND METHOD

(75) Inventor: Donald J. Geisel, Clifton Park, NY (US)

(73) Assignees: D. J. Geisel Technology, Inc.; Donald J. Geisel & Assoc., Inc.

( * ) Notice: Subject to any disclaimer, the term of this patent is extended or adjusted under 35 U.S.C. 154(b) by 0 days.

This patent is subject to a terminal disclaimer.

(21) Appl. No.: 10/159,675

(22) Filed: May 30, 2002

(65) Prior Publication Data

US 2002/0180460 A1 Dec. 5, 2002

Related U.S. Application Data

(63) Continuation-in-part of application No. 09/864,050, filed on May 23, 2001, now Pat. No. 6,400,161.

(51) Int. Cl.[7] .................... G01R 27/04; G01N 27/00; G01N 9/00
(52) U.S. Cl. .................... 324/640; 324/632; 324/71.1; 73/32 R
(58) Field of Search .................... 324/640, 632, 324/639, 642, 644, 647, 643, 637, 71.1; 342/22; 73/602, 32 R

(56) References Cited

U.S. PATENT DOCUMENTS

| | | | | |
|---|---|---|---|---|
| 4,616,425 A | * | 10/1986 | Burns | 34/389 |
| 4,626,773 A | * | 12/1986 | Kroeger et al. | 324/642 |
| 5,610,527 A | * | 3/1997 | Yamaguchi | 324/639 |
| 6,114,863 A | | 9/2000 | Krahn et al. | 324/664 |
| 6,400,161 B1 | * | 6/2002 | Geisel | 324/644 |
| 6,411,103 B1 | * | 6/2002 | Tobias et al. | 324/632 |

* cited by examiner

*Primary Examiner*—Anjan K. Deb
(74) *Attorney, Agent, or Firm*—Schmeiser, Olsen & Watts

(57) ABSTRACT

A material analyzing apparatus and associated method for analyzing. The apparatus comprises an analyzer body that contains a generally insulative material casing; a material analyzing circuitry that includes a transmitter, a receiver, and a control; an antenna system that includes a transmitting antenna, a receiving antenna, and a ground layer; a coupling structure that couples the antenna system to the material analyzing circuitry. The transmitter of the material analyzing circuitry generates a electromagnetic wave signal that is adapted to be sent by the transmitting antenna and directed into the material to be analyzed. The receiving antenna receiving any returned signal from the material and send the returned signal to the receiver and control. The control then analyzes the signal for material characteristics, including at least one of density, material segregation, and moisture.

20 Claims, 5 Drawing Sheets

MATERIAL SEGREGATION, DENSITY, AND MOISTURE ANALYZING APPARATUS AND METHOD

The present patent application is a continuation-in-part of U.S. patent application Ser. No. 09/864,050, filed May 23, 2001 now U.S. Pat. No. 6,400,161 and entitled "Material Segregation and Density Analyzing Apparatus and Method."

TECHNICAL FIELD OF INVENTION

The present invention relates generally to a material analyzing apparatus and method for measurement of density, segregation (i.e., non-uniformity), and moisture content of a test material.

BACKGROUND OF THE INVENTION

The invention relates to a material segregation and density analyzing apparatus and method to analyze density and segregation of a material. In particular, the invention relates to a material segregation and density analyzing apparatus and method to analyze at least one of density and segregation of asphalt.

Ninety-six percent of all paved roads and streets in the United states, almost two million miles, are surfaced with asphalt. Asphalt is a relatively low cost pavement material, especially in comparison to other pavement materials, such as concrete. Another asphalt feature that makes it superior to concrete for pavement is its flexibility. The maintenance of asphalt is also typically less expensive than maintaining concrete.

It is the nature of asphalt pavement to be non-uniform. It is very difficult to achieve a non-segregated and completely homogeneous asphalt mix for pavement. Also, the asphalt mix is very difficult to apply in an essentially uniform pavement layer. Therefore, the pavement is characterized by measurements in material variations and/or segregation. These variations or segregation are often visible on the pavement surface, however, it is a very subjective and difficult process for quantifying the pavement segregation amount. Pavement segregation is representative of pavement density.

Segregation can be defined as the separation of coarse and fine aggregate particles in the hot mix asphalt mixture. Alternately, segregation has been described as a separation and consolidation of the larger aggregate asphalt particles, which leave the asphalt mass and rise to the surface of the mix. This segregation can occur in the mixed material before it is fed onto the highway or it may become segregated as it is being placed onto the road surface. Research indicates that segregation has a direct impact on the long-term performance of the asphalt pavement by increasing the air void content of the mix, thus increasing the potential for moisture damage, raveling, cracking and a total disintegration of the affected road surface. Therefore, it is desirable to determine the pavement segregation.

When paving a particular highway, the asphalt mix, which is to be applied is routinely checked for mix properties at the asphalt mix plant. The check attempts to verify the asphalt mix integrity and homogeneity, and thus to control the ultimate density of the asphalt mix, when applied and rolled. The check of the asphalt mix can be correlated to resultant pavement density and segregation when applied. Accordingly, pavement specimens for control can be available for potential density device calibration or referencing of pavement density indicator devices.

When an asphalt paver lays a layer of asphalt mix for compaction on a highway, the asphalt quality will relate to the longevity of the new highway. Such longevity-influencing factors include, but are not limited to, density of the asphalt mix as it becomes compacted on a road surface and the homogeneity and segregation of the asphalt mix. Although the mix of liquid asphalt and rock aggregate segregation may have been ideal at the asphalt plant, there is no guarantee of the mix quality as applied to the road surface. The lack of homogeneity can be described as segregation.

Paving material (pavement) is typically laid down by a paver at about 75% of its desired compaction. During subsequent compaction, for example by being rolled over, it is very desirable to compact the paving material close to the final desired pavement compaction degree, without altering the segregation. The pavement compaction should be as close to the desired compaction to provide an absence of material variations, such as, but not limited to, air voids, which are believed to create defects in the resulting paved structure.

The level of pavement compaction cannot be readily determined without complicated measurements. These complicated pavement measurements may not be accurate. In the past, these complicated pavement measurements typically involved boring out of a portion of the rolled pavement (hereinafter also referred to as "extractions") and measuring their density in the lab. This process forms a hole in the pavement, which of course is not desirable. This hole is not desirable as the integrity of the pavement is breached.

In order to address these asphalt-related problems, various complicated asphalt pavement measurement systems and devices have been proposed and developed. For example, and in no way limiting of the invention, measurement of pavement dielectric properties has been proposed to determine pavement density, which has been suggested as an indicator of pavement compaction level.

One such known pavement density indicator device is disclosed in U.S. Pat. No. 3,784,905 to Blackwell. The Blackwell device appears to measures dielectric properties of the applied and rolled asphalt, in which the dielectric properties are believed to be representative of a change in pavement or asphalt density. The Blackwell device appears to operate at low frequencies where its operations are subject to variations in moisture and temperature, and thus can result in errors. While Blackwell may provide adequate operations in some instances, the Blackwell device must be moved at extremely slow speeds across the material being tested to obtain a density reading. Thus, it appears that the Blackwell device may need extended time periods of operation to provide a density determination, which as discussed above is not desirable. Further, the Blackwell device possesses a large weight, which may necessitate large supportive objects to support and transport the Blackwell device. The large objects may be dragged across the applied pavement surface, thus potentially causing damage to the often freshly-applied pavement.

Another potential disadvantage of the Blackwell device may be its limited depth adjustability for measurement. This limited depth adjustability may be attributed to the Blackwell electrodes only varying a depth of measurement by changing the height of the electrodes. This electrode configuration is not desirable due to the limited depth adjustability for measurement.

Another known pavement indicator device comprises a nuclear source, which is used to determine density of a pavement material. This nuclear-sourced device has a variety of drawbacks. Some of these drawbacks in the nuclear-sourced devices include that the nuclear-sourced device requires a licensed operator, controls, and a radiation shield (e.g., a lead enclosure). Of course, these nuclear-sourced device drawbacks lend to an increased cost of the nuclear-sourced device, increased cost of operation, and inherent dangers found with nuclear materials. Further, the nuclear-sourced device is non-adjustable for pavement area and depth, requires long time for, and is very heavy and difficult to maneuver. Furthermore, the nuclear-sourced device is also very expensive, at least in part due to the nuclear material of the nuclear-sourced device. Additionally, these nuclear density devices need to be constantly correlated to core densities that are taken from the same location as was nuclear gauge tested. This correlation should be done for each different mix that might be used. These steps are of course timely and cost consuming, and thus make use of these nuclear devices undesirable.

Another conventional pavement density indicator device is set forth in U.S. Pat. No. 5,900,736 assigned to TransTech Systems. The TransTech System pavement density indicator device is a non-nuclear, asphalt density measuring device. The TransTech System pavement density indicator device appears to be based on electric field or capacitance.

Recently, current developments in paving technology have allowed pavement to be applied in thinner layers, as compared to the pavement layers applied in the past. This thinner pavement reduces the amount of pavement that can be bored from rolled pavement, for example for a test core (described hereinafter). Accordingly, a need exists for a reliable, convenient pavement density, compaction, and segregation degree determining device, in which the device functions with desired results in which the top area of the pavement does not adversely influence the operation of an apparatus and method to analyze density and segregation of a material, especially if used on pavement, which is applied in thick or thin layers.

Further, the application of pavement may vary dependent on the pavement's underlying base structure, thus resulting in differing depths, areas, shapes, and volumes of the pavement. Of course, it is desirable to determine the density, compaction, and segregation degree of such pavement. Therefore, it is desirable to provide a pavement density, compaction, and segregation degree determining device that is capable of pavement density measurement at differing depths, areas, shapes, and volumes of the pavement.

Furthermore, the operation of conventional apparatus that attempt to measure the density, compaction, and segregation degree of pavement is often slow and requires complicated operations for appropriate device functionality. This lack of speed is often adverse to the determination of pavement density and compaction. Thus, the measure of density, compaction, and segregation degree is typically a tedious and drawn-out process that slows down the ultimate pavement application operation. Accordingly, a need exists to provide an asphalt pavement density analyzer or convenient pavement density, compaction, and segregation degree determining device that can determine pavement density in a faster, more convenient process than those currently available.

Yet another potential disadvantage of the conventional pavement density indicator devices may be found in an inability to move to various configurations, such as in shape and area. The conventional devices often do not permit movement or alteration of the sensing area, and are not configured to readily permit the pavement density indicator device to be moved to determine density and compaction.

Accordingly, a need exists for a pavement density indicator device that can determine pavement density in particular configurations of pavement.

SUMMARY OF THE INVENTION

The invention is directed to an apparatus to analyze density and segregation of a material. The material analyzing apparatus comprises an analyzer body that comprises a generally insulative material casing; a material analyzing circuitry that includes a transmitter, a receiver, and a control; an antenna system that comprises a transmitting antenna, a receiving antenna, and a ground layer; a coupling structure that couples the antenna system to the material analyzing circuitry. The transmitter of the material analyzing circuitry generates a VHF electromagnetic wave signal that is adapted to be sent by the transmitting antenna and directed into the material to be analyzed. The receiving antenna receiving any returned signal from the material and sent to the receiver and to the control. The control then able to analyze the signal for material characteristics.

Further, the invention sets forth a material analyzing apparatus. The material analyzing apparatus comprises an analyzer body that comprises a generally insulative material casing; a material analyzing circuitry that includes comprising a transmitter, a receiver, and a control; an antenna system that comprises a transmitting antenna, a receiving antenna, and a ground layer; a coupling structure that couples the antenna system to the material analyzing circuitry. The transmitter of the material analyzing circuitry generates a VHF electromagnetic wave signal that is adapted to be sent by the transmitting antenna and directed into the material to be analyzed. The receiving antenna receiving any returned signal from the material and sent to the receiver and to the control. The control then able to analyze the signal for material characteristics. The material characteristics including at least one of density and material segregation.

The invention is directed to an apparatus to analyze density and segregation of a material. The material analyzing apparatus comprises an analyzer body that comprises a generally insulative material casing; a material analyzing circuitry that includes comprising a transmitter, a receiver, and a control; an antenna system that comprises a transmitting antenna, a receiving antenna, and a ground layer; a coupling structure that couples the antenna system to the material analyzing circuitry. The transmitter of the material analyzing circuitry generates a VHF electromagnetic wave signal that is adapted to be sent by the transmitting antenna and directed into the material to be analyzed. The receiving antenna receiving any returned signal from the material and sent to the receiver and to the control. The control then able to analyze the signal for material characteristics. Density of the material can be linearly related to a returned signal. The control can determine density D being generally equal to a measured returned voltage V times a constant slope m, plus an offset b, in accordance with:

$$D = m \times V + b.$$

The invention is directed to an apparatus to analyze density and segregation of a material. The material analyzing apparatus comprises an analyzer body that comprises a generally insulative material casing; a material analyzing circuitry that includes a transmitter, a receiver, and a control; an antenna system that comprises a transmitting antenna, a receiving antenna, and a ground layer; a coupling structure that couples the antenna system to the material analyzing circuitry. The transmitter of the material analyzing circuitry generates a VHF electromagnetic wave signal that is adapted to be sent by the transmitting antenna and directed into the material to be analyzed. The receiving antenna receiving any returned signal from the material and sent to the receiver and to the control. The control then able to analyze the signal for material characteristics. The control then able to analyze the signal for material characteristics, the material segregation of $$SL = k \int_{s1}^{s2} |\Delta\rho/\Delta s|$$

where k is a constant, ρ is pavement density and s is distance across a surface.

A further aspect of the invention provides a method for analyzing a material. The method comprises providing an analyzer body, the analyzer body comprising a generally insulative material casing; providing material analyzing circuitry, the material analyzing circuitry comprising a transmitter, a receiver, and a control; providing an antenna system, the antenna system comprising a transmitting antenna, a receiving antenna, and a ground layer; coupling antenna system to the material analyzing circuitry; and generating a VHF electromagnetic wave signal; transmitting the VHF electromagnetic wave signal by the transmitting antenna; directing the signal to be analyzed; receiving any returned signal from the material; sending the returned signal to the receiver and control; and analyzing the signal for material characteristics.

A material analyzing apparatus for measuring material segregation. The apparatus comprising analyzer body, the analyzer body comprising a generally insulative material casing; material analyzing circuitry, the material analyzing circuitry comprising a transmitter, a receiver, and a control, an antenna system, the antenna system comprising a transmitting antenna, a receiving antenna, and a ground layer; a coupling structure that couples the antenna system to the material analyzing circuitry. The transmitter of the material analyzing circuitry generates a VHF electromagnetic wave signal, the VHF electromagnetic wave signal being adapted to be sent by the transmitting antenna, being directed into the material to be analyzed, the receiving antenna receiving any returned signal from the material and then sent to the receiver and to the control, the control then able to analyze the signal for material characteristics, the material segregation (Seg or Segregation Level) being determined by: Seg=constant×SD+offset, where SD is the standard deviation of measurements.

A further aspect of the invention provides a method for analyzing a material. The method comprises providing an analyzer body, the analyzer body comprising a generally insulative material casing; providing material analyzing circuitry, the material analyzing circuitry comprising a transmitter, a receiver, and a control; providing an antenna system, the antenna system comprising a transmitting antenna, a receiving antenna, and a ground layer; coupling antenna system to the material analyzing circuitry; and generating a VHF electromagnetic wave signal; transmitting the VHF electromagnetic wave signal by the transmitting antenna; directing the signal to be analyzed; receiving any returned signal from the material; sending the returned signal to the receiver and control; and analyzing the signal for material characteristics. The step of analyzing the signal for material segregation characteristics can be determined by $$SL = k \int_{s1}^{s2} |\Delta\rho/\Delta s|$$

where k is a constant, ρ is pavement density and s is distance across a surface.

A further aspect of the invention provides a method for analyzing a material. The method comprises providing an analyzer body, the analyzer body comprising a generally insulative material casing; providing material analyzing circuitry, the material analyzing circuitry comprising a transmitter, a receiver, and a control; providing an antenna system, the antenna system comprising a transmitting antenna, a receiving antenna, and a ground layer; coupling antenna system to the material analyzing circuitry; and generating a VHF electromagnetic wave signal; transmitting the VHF electromagnetic wave signal by the transmitting antenna; directing the signal to be analyzed; receiving any returned signal from the material; sending the returned signal to the receiver and control; and analyzing the signal for material characteristics. the density of the material being linearly related to a returned signal, and determining density D being generally equal to a measured returned voltage V times a constant slope m, plus an offset b, in accordance with:

$$D=m \times V+b.$$

A further aspect of the invention provides a material analyzing apparatus for measuring material segregation. The apparatus comprises an analyzer body that comprises a generally insulative material casing; material analyzing circuitry that comprises a transmitter, a receiver, and a control; an antenna system, in which the antenna system comprises a transmitting antenna, a receiving antenna, and a ground layer; a coupling structure that couples the antenna system to the material analyzing circuitry. The transmitter of the material analyzing circuitry generates a VHF electromagnetic wave signal. The VHF electromagnetic wave signal being adapted to be sent by the transmitting antenna, and is directed into the material to be analyzed. The receiving antenna receiving any returned signal from the material and then sending same to the receiver and to the control. The control is then able to analyze the signal for material characteristics. The material segregation (Seg) being determined by Seg=constant×SD+offset, where SD is the standard deviation of measurements.

A yet further aspect of the invention sets forth a method for measuring material segregation. The method comprises providing an analyzer body comprising a generally insulative material casing; providing material analyzing circuitry comprising a transmitter, a receiver, and a control; providing an antenna system comprising a transmitting antenna, a receiving antenna, and a ground layer; coupling the antenna system to the material analyzing circuitry; generating a VHF electromagnetic wave signal; transmitting the VHF electromagnetic wave signal by the transmitting antenna; directing the signal to be analyzed; receiving any returned signal from the material; sending the returned signal to the receiver and control; and analyzing the signal for material segregation characteristics. The determining material segregation (Seg) is by Seg=constant×SD+offset, where SD is the standard deviation of measurements.

DESCRIPTION OF THE INVENTION

Figure 1:
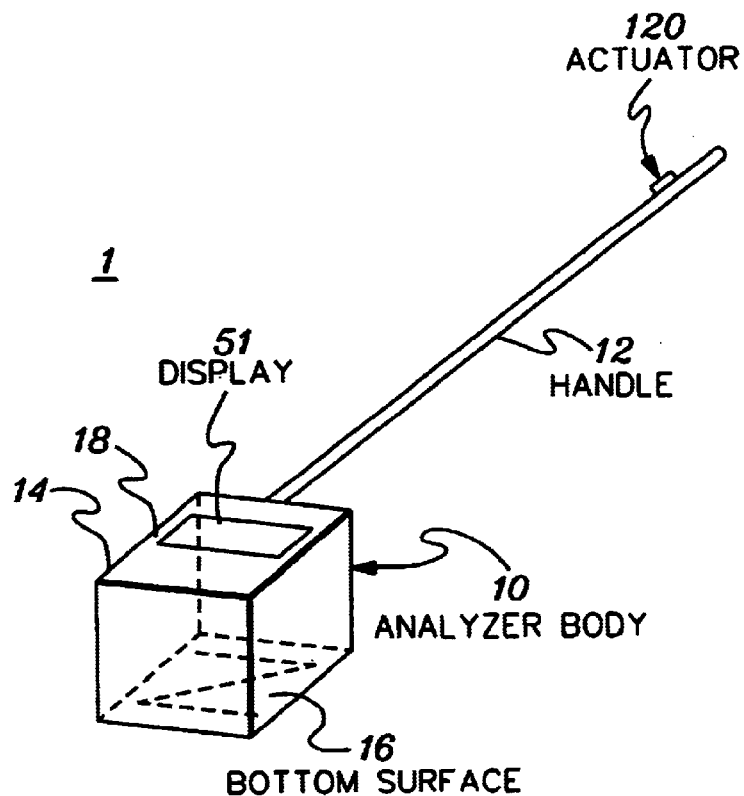
FIG. 1 is a schematic illustration of a material segregation and density analyzing apparatus, as embodied by the invention.

The invention comprises a material segregation and density analyzing apparatus and method (hereinafter "material analyzing apparatus") to analyze density and segregation of a material. For example, the invention comprises a material analyzing apparatus for measuring and determining at least one of density, compaction and segregation of asphalt. The asphalt may be recently applied asphalt.

The material analyzing apparatus, as embodied by the invention, comprises a portable material analyzing apparatus. The term portable as used in this context means that the material analyzing apparatus can be easily moved by a standing operator of the material analyzing apparatus, in operations as described herein.

The material analyzing apparatus, as embodied by the invention, can be supported by the user of the material analyzing apparatus. For example and in no way limiting of the invention, the material analyzing apparatus may be utilized as a hand-held material analyzing apparatus. The material analyzing apparatus, as embodied by the invention, can be placed on a target test location, on a newly paved highway to measure density of the asphalt. The measurement may be taken in any appropriate units, such as, but not limited to, in pounds per cubic foot.

The material analyzing apparatus 1 (FIG. 1), as embodied by the invention, is relatively light-weight (such as approximately ¾–1 pound) with a relative perimeter size body and base (also known as a "foot") of about 5 inches by about 5 inches. These configurations and weights are merely exemplary of the size, shape and weights of the material analyzing apparatus as embodied by the invention, and are not intended to limit the invention in any manner. The material analyzing apparatus may comprise any configurations and weights as long as the functionality and operations of the material analyzing apparatus are maintained.

The material analyzing apparatus 1, as embodied by the invention, comprises a "relative" reading device. The term relative reading device as used in this specification means that the material analyzing apparatus should be calibrated to a known density material. This calibration or referencing of the material analyzing apparatus typically occurs prior to use at a paving location.

The material analyzing apparatus 1 is a portable unit for making a density and segregation measurement. (In the following description of the material analyzing apparatus, as embodied by the invention, will refer to one or both of the density and segregation measurements, and the use of one implies the use of the other). The device relies on technology for penetration into the asphalt mat for density measurement. The segregation measurement is, however, different from a simple density measurement, in that, a segregation level is calculated from numerous density measurements automatically by the device, presenting the user with a number, segregation level and along with density. Further, the material analyzing apparatus, as embodied by the invention, utilizes VHF electromagnetic wave signals directed into the pavement, in which the high frequencies can comprise, but are not limited to, VHF signals. This type of VHF electromagnetic wave signals are intended to be exemplary of the signals within the scope of the invention, and are not intended to limit the invention in any manner. The following description will refer to the VHF electromagnetic wave frequencies.

Figure 3:
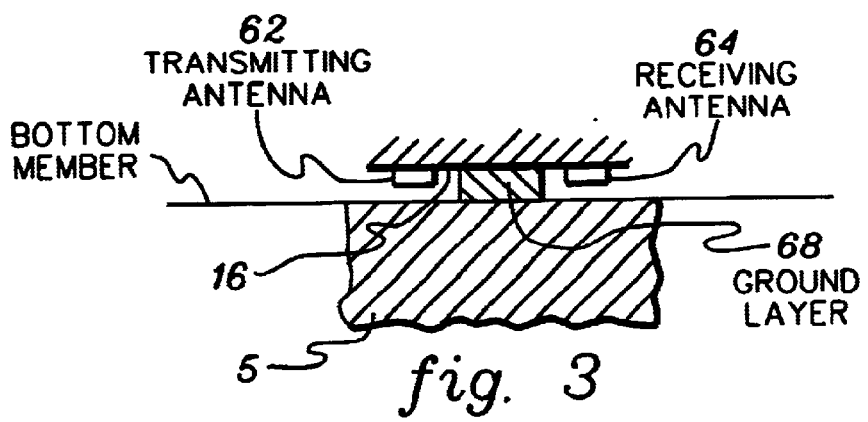
FIG. 3 is a schematic illustration of the antenna for the material segregation and density analyzing apparatus, as embodied by the invention.
Figure 2:
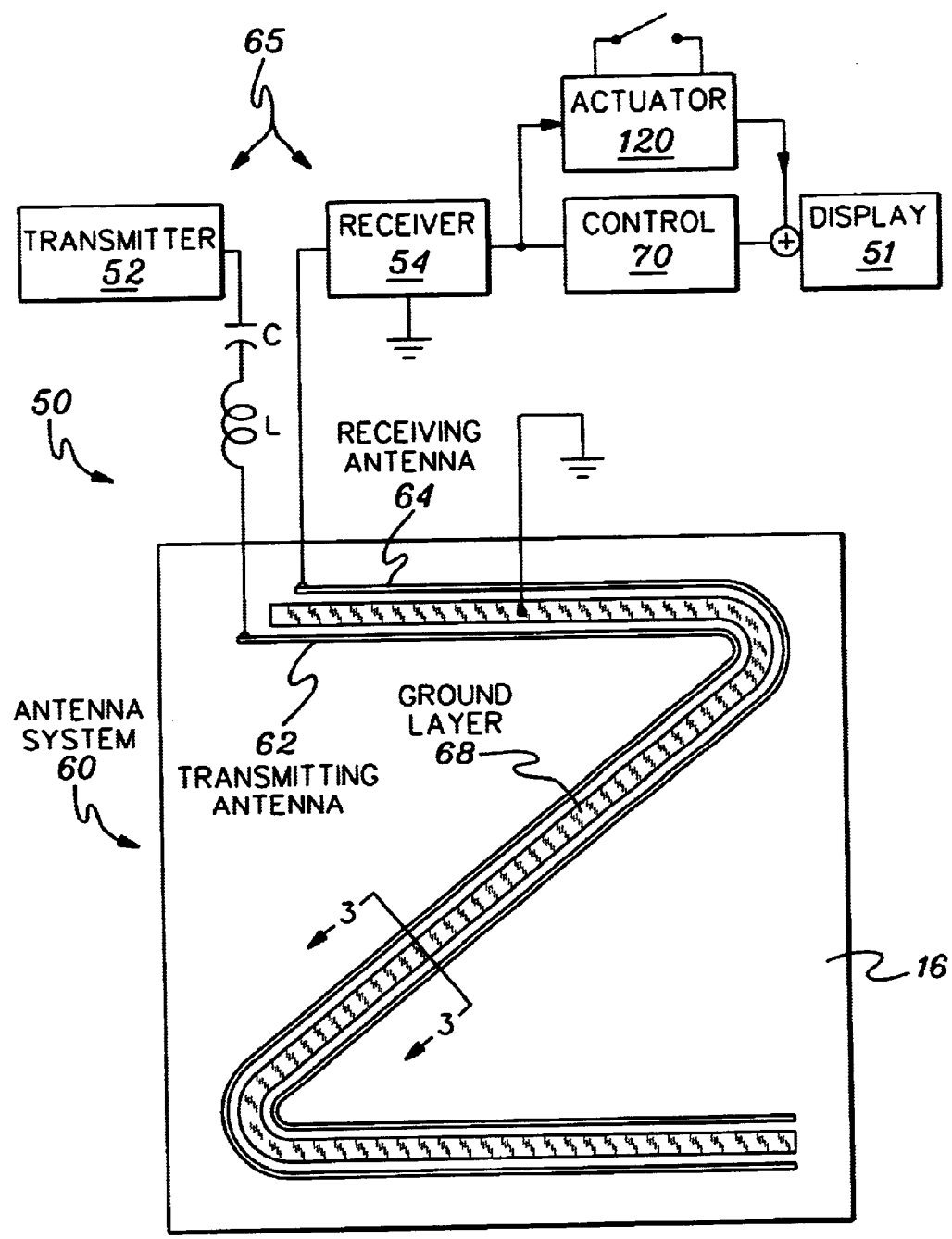
FIG. 2 is a schematic illustration of the circuitry for the material segregation and density analyzing apparatus, as embodied by the invention.

The material analyzing apparatus, as embodied by the invention, is schematically illustrated in FIGS. 1–3. The material analyzing apparatus 1 in FIG. 1 comprises an analyzer body 10 and a handle 12. The handle 12 can be used to maneuver and manipulate the material analyzing apparatus 1 for pavement analysis, as described herein. The handle 12 comprises at least a portion thereof that is non-conductive or insulating. For example, and in no way limiting of the invention, the handle 12 can comprise insulating material for the first portion, for example the first 12 inches of the handle, and the remaining portion may be formed of any material. The above is merely an example and the scope of the invention includes any other structure and configuration of the handle. The analyzer body 10 can comprise the configuration as described above.

The analyzer body 10 comprises a generally insulative material casing 14 in which the material analyzing apparatus 1 circuitry 50, as described hereinafter, is disposed. The analyzer body 10 comprises a base or bottom surface 16 that is formed of a non-metallic material. The bottom surface 16 of the analyzer body 10 is formed of a non-metallic material in order to prevent interference and shielding of the circuitry 50 of the material analyzing apparatus 1.

The top surface 18 of the analyzer body 10 of the material analyzing apparatus 1 includes at least one display 51, which is connected to the circuitry 50 of the material analyzing apparatus 1. The at least one display 51 is used to provide real-time or near real-time indicia of the analysis by the material analyzing apparatus 1 to the operator or user of the material analyzing apparatus 1. The at least one display 51 can also provide indicia of at least one of density, compaction and segregation of asphalt as determined by the material analyzing apparatus 1. The method of providing results for the material analyzing apparatus 1 using the display 51 may be provided as the sole method of providing results to the user or operator of the material analyzing apparatus 1, and in the alternative, the method of providing results for the material analyzing apparatus 1 using the display 51 may be provided in combination with a communication link configuration, which will be described in detail hereinafter.

The material analyzing apparatus 1, as embodied by the invention, can include a secondary data transmitter to send signals generated by the material analyzing apparatus 1. The signals generated and sent by the material analyzing apparatus 1 may be received by any appropriate receiver, such as but not limited to, a computer, for example via a modem or wireless modem. These are merely exemplary and not intended to limit the invention in any manner. The receiver may be located in close proximity to the pavement being analyzed by the material analyzing apparatus 1. If the transmitter systems (not illustrated) of the material analyzing apparatus 1 is of sufficient power, the receiver need not be located in close proximity to the pavement being analyzed by the material analyzing apparatus 1. Regardless of the location of the receiver to the pavement being analyzed by the material analyzing apparatus 1, the material analyzing apparatus 1 can send signals generated by the material analyzing apparatus 1 to a receiver that is remote from the material analyzing apparatus 1.

The insulating handle 12 of the material analyzing apparatus 1 comprises a structure that can allow a user or operator of the material analyzing apparatus 1 to easily maneuver the material analyzing apparatus 1 for use. The insulating handle 12 can be used to move the material analyzing apparatus 1 for determination of at least one of density, compaction and segregation in operation. The insulating handle 12 may comprise an actuator 120 that is in a position on the insulating handle 12 for easy reach by an operator or user of the material analyzing apparatus 1.

The actuator 120 can be used to operate the circuitry 50 of the material analyzing apparatus 1 so that at least one of density, compaction and segregation of pavement can be determined. The actuator 120 can operate the circuitry 50, be used for the calibration or referencing of the material analyzing apparatus 1, as described herein, and send signals representative of at least one of density, compaction and segregation of the pavement from the operation of the material analyzing apparatus 1, as embodied by the invention.

The material analyzing apparatus 1, as embodied by the invention, comprises a circuitry 50 that is used for determination of at least one of pavement density, compaction and segregation. The circuitry 50 of the material analyzing apparatus 1 is disposed in the generally insulative material casing 14 of the material analyzing apparatus 1. The circuitry 50 is operable to emit signal in a simple continuous wave, for example, but in no way limiting the invention, a signal in a simple continuous wave at about 50 MHz.

The material analyzing apparatus 1, as embodied by the invention, can include a bottom member (not illustrated for ease of illustration purposes). The bottom member comprises a structure that protects the bottom structure of the material analyzing apparatus 1. The bottom member protects the material analyzing apparatus 1 from abrasion during use, for example as the material analyzing apparatus 1 is moved across pavement in operation of the material analyzing apparatus 1, as embodied by the invention. The bottom member can comprise any non-conductive and non-interfering material, such as but not limited to, rubber, synthetic materials (LEXAN), and other such materials. The bottom member can comprise a flexible member that is attached to the material analyzing apparatus 1 analyzer body 10, for example attached by VELCRO or other such attaching member. The bottom member should be sufficiently thin to not interfere with generation and return of signals. For example, and in no way limiting of the invention, the bottom member can be about 10 mil thick.

FIG. 2 illustrates details of the circuitry 50. The circuitry 50 comprises a transmitter 52 and a receiver 54. The simple continuous wave at about 50 MHz that is generated by the circuitry 50 can originate from the transmitter 52, such as, but not limited to, a micro-power transmitter 52 and the receiver 54. The receiver 54 can be provided with a with a tuned diode detector. The transmitter 52 and a receiver 54 can each be mounted in the analyzer body 10 of the material analyzing apparatus 1.

The circuitry 50 of the material analyzing apparatus 1, as embodied by the invention, further comprises an antenna system 60. The antenna system 60 is disposed on the material analyzing apparatus 1 and is typically is in contact with the pavement 5 (FIG. 3) during operation of the material analyzing apparatus 1. The antenna system 60 comprises a transmitting antenna 62 that is in connectivity with the transmitter 52. The antenna system 60 also comprises a receiving antenna 64 that is in connectivity with the receiver 54.

The connectivity between the transmitting antenna 62 and the transmitter 52 and between the receiving antenna 64 and the receiver 54 can be done by any appropriate means, such as illustrated with a coupling structure 65. The coupling structure 65 between transmitting antenna 62 and the transmitter 52 and between the receiving antenna 64 and the receiver 54 can comprise straight hard line wiring as illustrated. The coupling structure 65 wiring for the transmitting antenna 62 and the transmitter 52 and between the receiving antenna 64 and the receiver 54 may also include various electrical components, such as a capacitor and inductor (as illustrated). The illustrated configuration and those described herein are merely illustrative of the material analyzing apparatus 1, as embodied by the invention, and are not intended to be limiting of the invention. Other features of the invention are within the scope if the invention.

The antenna system 60 of the circuitry 50 in the material analyzing apparatus 1, (FIG. 1) as embodied by the invention, can emit a radio frequency, electromagnetic wave (E×H), where E is the electric field and H is the magnetic field. Further, permativity (dielectric) and permeability of the material under test affect the propagation of both E and H field components, respectively. The radio frequency, electromagnetic wave (as used herein as "signal") is emitted into the into the pavement 5 from the transmitting antenna 62. The receiving antenna 64 can picks up or receives the signal as it return from the pavement 5.

The antenna system 60 comprises the transmitting antenna 62 and the receiving antenna 64. The transmitting antenna 62 and the receiving antenna 64 form a 2-conductor transmission line. The 2-conductor transmission line is bent into the general configuration of a "Z" (two parallel segments and a diagonal segment connecting opposite ends of the two parallel segments), however, this description of the 2-conductor transmission line is exemplary of many other configurations that the 2-conductor transmission line, as embodied by the invention, can be formed. This description is not intended to limit the invention in any manner.

The material analyzing apparatus 1 attempts to make contact between the antenna system 60 and the pavement 5. This amount of contact can be thought of as maximizing surface contact between the pavement 5 and the antenna system 60 of the material analyzing apparatus 1, including coverage at the mid-portion of the base or bottom surface 16.

Noting the configuration of the antenna system 60 on the base or bottom surface 16, the 2-conductor transmission line portion of the antenna system 60 is intended to lie flat on pavement 5. The transmitting antenna 62 and the receiving antenna 64 are disposed in a generally parallel relationship to each other. The strength of the signal, which is generated by the transmitting antenna 62 and received by the receiving antenna 64 is directly proportional to the pavement density.

The antenna system 60, as embodied by the invention, further comprises a ground layer 68. The ground layer 68 is disposed further the transmitting antenna 62 and the receiving antenna 64 in a generally parallel orientation between the transmitting antenna 62 and the receiving antenna 64. The ground layer 68 is the "middle" of the Z, in which the transmitting antenna 62 and the receiving antenna 64 form the outer sides of the Z, in a manner to sandwich the ground layer 68 therebetween.

The ground layer 68 is also positioned on the base or bottom surface 16 of the body 14 of the material analyzing apparatus 1, as illustrated in FIG. 1. The ground layer 68 extended from the base or bottom surface 16 a first distance and the transmitting antenna 62 and the receiving antenna 64 extend from the base or bottom surface 16 a second distance. The first distance is greater than the second distance, so the ground layer 68 extends further from the base or bottom surface 16 more than the transmitting antenna 62 and the receiving antenna 64. Therefore, signals, both the E and H components entering and leaving the pavement 5 favor deeper portions of the pavement 5. These signals have a lesser tendency to be adversely effected by the pavement 5 near the pavement's surface. Thus, this configuration results in return signals being less effected by the surface properties, characteristics, and configurations of pavement. For example, and in no way limiting of the invention, the ground layer 68 can be up to about 0.030" closer to the pavement 5 than the transmitting antenna 62 and the receiving antenna 64. This orientation and configuration can cause the first about 0.125" of pavement not to signals to the material analyzing apparatus 1. This ignoring effect is desirable because surface anomalies and unwanted surface moisture from paving operations can corrupt density readings.

The material analyzing apparatus 1 comprises a relative reading instrument, which is described hereinafter. The paving industry has standardized on 6-inch diameter test cores, which are extracted from highways. Additionally, such cores can be made in the lab from a pavement mix to determine the maximum theoretical density of a particular mix. The cores are used to provide standardized readings for least one of density, compaction and segregation of pavement. For example, when paving a road, the asphalt mix is checked daily at the asphalt plant, as this check may be a contractual requirement. Hence these cores or specimens are available for density (and compaction and segregation) for the material analyzing apparatus 1 calibration. The material analyzing apparatus 1, as embodied by the invention is small enough in size to calibrate the industry standard 6-inch diameter test cores. Prior devices are not believed to be small enough to be able to calibrate the industry standard 6-inch diameter test cores.

The material analyzing apparatus 1, as embodied by the invention, further has a reference feature, which can allow a user or operator to calibrate the material analyzing apparatus 1 to a reference standard prior to each field measurement. This calibration or reference feature is included in the circuitry 50, and can be controlled by the actuator 120 of the insulating handle as discussed above. The reference feature, as embodied by the invention, permits the reference of the material analyzing apparatus 1 with enhanced speed and high repeatability.

The reference feature, as described above, will be further described with reference to FIG. 2. In FIG. 2, the transmitter 52 is coupled to the antenna system 60, for example connected by a non-resonant LC at the coupling structure 65. The coupling structure 65 can comprise a tuned coupling structure for the receiving functionality of the material analyzing apparatus 1. The detector 54 can comprise single diode detector, which is used for conversion of signals to direct current (DC).

In operation of the reference feature, signals are converted to a direct current and compared to an internal reference signal. The internal reference signal can be stored on a memory or in a control in the material analyzing apparatus 1. Alternatively, the internal reference signal may be stored in a remote memory, such as, but not limited to, to a memory stored in a computer to which the material analyzing apparatus 1 can communicate.

The calibration of the material analyzing apparatus, (which is distinctly different from the reference that is discussed above) as embodied by the invention, can be conducted by at least two methods. A first calibration method, as embodied by the invention, comprises taking highway data using the material analyzing apparatus, as embodied by the invention and also taking cores from the pavement. Next, in a laboratory, the cores are analyzed for at least one of density, compaction and segregation. Thereafter, a gauge of the material analyzing apparatus, as embodied by the invention, can be set to read correctly based on this core data.

A second calibration method comprises using the material analyzing apparatus, as embodied by the invention, to evaluate and analyze test cores prepared in a laboratory, in which the cores are prepared using a vibratory compaction of asphalt from an earlier asphalt mix, which can be sampled from the asphalt plant. The material analyzing apparatus, as embodied by the invention, be placed directly over the laboratory cores. Thus, the material analyzing apparatus can be used to calibrate in rapid or approximate real-time, to the asphalt mix being put down as pavement. Several departments of transportation (DOT) and the Federal DOT have indicated that this approach would be desirable for calibration purposes.

It will be appreciated by those skilled in the art that the control 70 can also be implemented using a variety of separate dedicated or programmable integrated or other electronic circuits or devices, such as hardwired electronic or logic circuits including discrete element circuits or programmable logic devices, such as PLDs, PALs, PLAs or the like. The control 70 can also be implemented using a suitably programmed general-purpose computer, such as a microprocessor or microcontrol, or other processor device, such as a CPU or MPU, either alone or in conjunction with one or more peripheral data and signal processing devices. In general, any device or similar devices on which a finite state machine capable of implementing the flow charts, as illustrated in the application, can be used as the control. As shown a distributed processing architecture is a preferred for maximum data/signal processing capability and speed.

In operation, the material analyzing apparatus 1, as embodied by the invention, can be used to make a pavement segregation measurement. The pavement segregation measurement using the material analyzing apparatus 1 can be achieved by placing the material analyzing apparatus 1 on a pavement surface, actuating the circuitry 50 of the material analyzing apparatus 1, sending and receiving a signal, analyzing the signal, and displaying a pavement segregation measurement value for the operator.

The density-measuring function of the material analyzing apparatus 1 can include using the material analyzing apparatus 1, as embodied by the invention, to make at least one pavement density measurement. To use the material analyzing apparatus 1 to determine a cross-sectional analysis of pavement, multiple measurements of pavement density can be taken and averaged. This averaging is desirable because the pavement, regardless of how carefully it is applied is non-uniform.

The measurements are generally taken by moving, such as by rotating or traversing the material analyzing apparatus 1 about pavement. The number of measurements will vary, for example, in a range from about 4 density measurements to about 8 density measurements. The standard deviation of density measurements about a given location relates directly to the material segregation in the pavement.

For exemplary purposes, and not intended to limit the invention, in pavement with anticipated high segregation, a standard deviation for a pavement area will be high, such as, but not limited to, over about 3.0. For low segregation pavement or uniform pavement areas have a relatively low standard deviation, about 1.0. These standard deviation because the density values group closer together. The display of the material analyzing apparatus 1, as embodied by the invention, indicates a segregation that is derived from the density standard deviation of a pavement group that is being tested.

Operations of the material analyzing apparatus 1, as embodied by the invention, will now be described. The operation will describe operation for the material segregation and density analyzing apparatus and method, as embodied by the invention, to analyze density and segregation of a material. In particular, the operation will describe operation for the material segregation and density analyzing apparatus and method, as embodied by the invention, to analyze density and segregation of pavement. The following description of the operation of the invention is intended to merely describe exemplary operations of the invention, and are not intended to limit the invention in any manner. As will be evident, other operations are within the scope of the invention.

In operation to determine segregation levels of pavement, the material analyzing apparatus 1, as embodied by the invention provides for analysis by the control 70 of the material analyzing apparatus 1 of the generated pavement density signals. The segregation is proportional to the standard deviation of density values. Accordingly, Segregation level=$k$×density Standard Deviation, where k is a constant.

Figure 4:
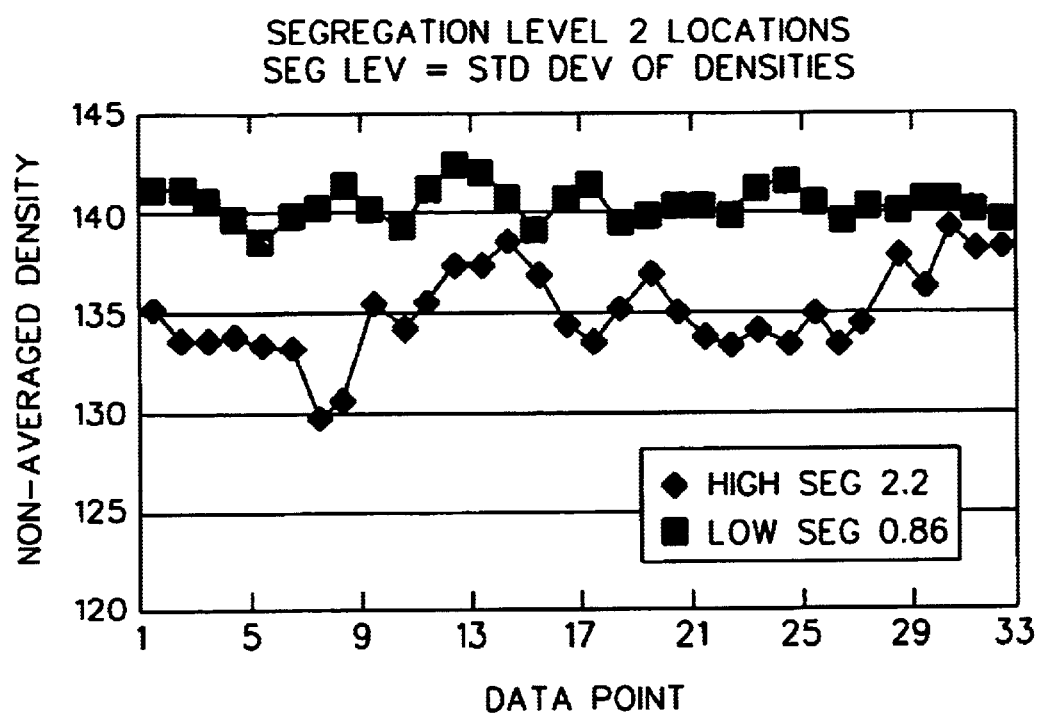
FIG. 4 a graph of non-averaged density versus pavement locations.

An example of the use and operation of the material analyzing apparatus 1, as embodied by the invention, comprises making multiple density measurements at a number of test locations. A spreadsheet software program with math functionality (such as EXCEL) can then be used to calculate standard deviations. In a first step, multiple density measurements at 2 separate locations. Location 1 had high visual segregation and location 2 had low visual segregation. The multiple measurements can be provided by rotating the material analyzing apparatus 1, as embodied by the invention, about a circular periphery geometry. FIG. 4 illustrates a graph that shows the data obtained from such an operation. As evidenced by the graph, the standard deviation at the high segregation location is about 2.2, or about 2.6 times the low segregation location, which is about 0.86.

Figure 5:
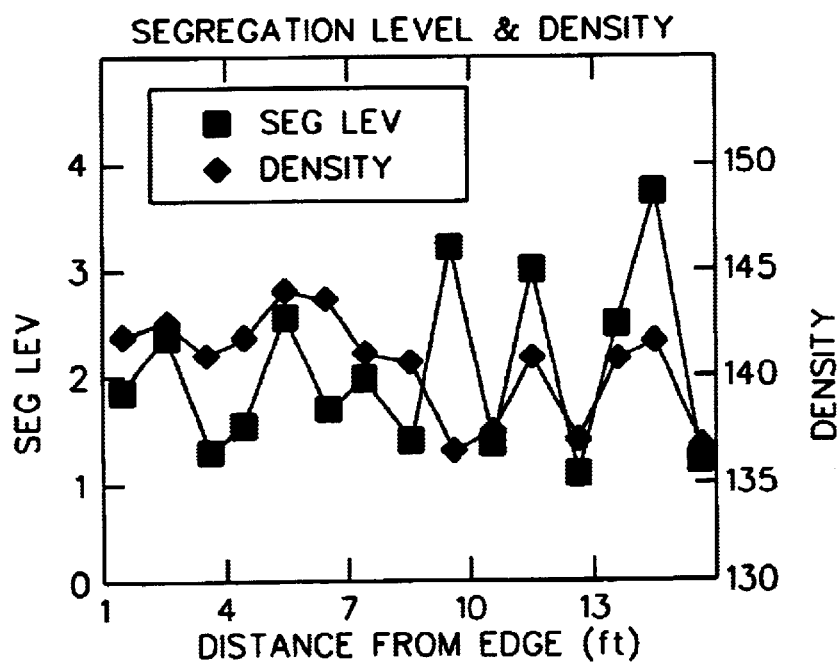
FIG. 5 a second graph of non-averaged density versus pavement locations.

Next, a profile was taken across pavement, slightly over 15 feet wide in length. The material analyzing apparatus 1, as embodied by the invention, recorded multiple density values at 1-foot increments. For each group of measured densities, the standard deviation and average density were calculated and plotted in FIG. 5. The graphs illustrate segregation level is on the left vertical axis and density on the right axis.

A material analyzing apparatus measurement system and associated operation using the material analyzing apparatus 1, as embodied by the invention, will now be further described. The measurement system and associated operation using the material analyzing apparatus 1 comprises at least 2, and in other embodiments at least one 4, material analyzing apparatus 1 units. The material analyzing apparatus 1 can be arranged in an appropriate configuration. This configuration can be is placed over a pavement area of unknown segregation. Multiple measurements, such as, but not limited to, four measurements of density can be made. The measurements may be made simultaneously. These measurements are used to determine at least one of a standard deviation and average value of density.

The determination can be calculated by the control 70 of the circuitry 50 of the material analyzing apparatus 1, as embodied by the invention. From these value determinations, a density standard deviation can be calculated by the control 70, and the density standard deviation can be displayed on the display 51 of the insulative material casing 14. Each material analyzing apparatus 1 of the set of material analyzing apparatus 1, as described above, can be rapidly moved from pavement location to pavement location. This movement can provide a readout of both segregation and average density. By this methodology, the separate material analyzing apparatus 1 units are equivalent to manually rotating a single material analyzing apparatus 1 unit to examine different volume sections of the pavement.

Multiple density values can be determined to calculate pavement segregation. The material analyzing apparatus 1 can be moved, for example, but not limited to, with at least one of one's hand or other simple mechanical means. The movement could be rotational or longitudinal. Using this methodology, the generated signal could comprise a density level plus density variation (DC+AC) as the material analyzing apparatus 1 is moved. First, the generated signal would be AC coupled to provide a density variation, then the generated signal would be full wave rectified and filtered, thus producing a DC level. The DC level is proportional to density variation.

This analog processing by the material analyzing apparatus 1, as embodied by the invention, can produce a generated signal that is proportional to segregation. The generated signal that is proportional to segregation would be displayed for the user. A toggle switch, which can be associated with the actuator, would allow the user or operator to switch between segregation and density modes.

The material analyzing apparatus 1, as embodied by the invention, is not adversely influenced by moisture and temperature, in direct contradiction of some known devices in the prior art. The material analyzing apparatus 1 and its operation is not adversely influenced because the signals are generated by the material analyzing apparatus 1 at very high frequencies or VHF electromagnetic wave. An exemplary frequency is about 50 Mhz. At this general frequency, the signal or field created by the material analyzing apparatus 1, as embodied by the invention, is actually an electromagnetic field. The material analyzing apparatus 1 transmits a signal into one side of the antenna system 60, while the received/returned signal is received by the opposite side of the antenna system 60. The received signal is detected by the receiver, whose output is a direct current signal, which is directly proportional to asphalt density.

Further, the antenna system 60, in the Z-shape is a uniform configuration. The antenna system 60 does not have a dead zone in its center due to the configuration. A dead zone, which is exhibited in prior art analyzing devices circular arrays tend to ignore an important pavement area. The electromagnetic field, which is also generated by the material analyzing apparatus 1, as embodied by the invention and discussed above, is governed by both Maxwell's and Poynting's equations, where a propagating wave is affected by both medium permittivity (dielectric) and permeability.

For example, the material analyzing apparatus 1, as embodied by the invention, can determine density of the materials, such as but not limited to pavement, by generating a VHF electromagnetic wave field. The field is passed through the material to measure its density. The density is linearly related to a measured return/returned signal that is measured as a voltage. The density D can be determined as being equal to the measured voltage V times a constant slope m, plus an offset b, as follows:

$$D = m \times V + b$$

As discussed above, moisture and temperature do not influence the material analyzing apparatus 1.

The material analyzing apparatus 1, as embodied by the invention, that generates VHF electromagnetic wave energy, which has capability to measure the material segregation of a test surface, in particular asphalt pavement. A segregation measurement method where the material segregation level (Seg of Segregation Level) can be determined suing a statistical standard deviation (SD) of approximately 7 or more density measurements about a test location. Thus the segregation level equals a constant times the standard deviation plus some offset, as follows:

$$SL = const. \times SD + \text{offset}.$$

Further, material analyzing apparatus 1, as embodied by the invention, that generates VHF electromagnetic wave energy, has capability to measure the material segregation of a material, such as but not limited to, pavement and asphalt. A further segregation measurement method, as embodied by the invention, can determine segregation level (SL) (also known as material segregation) as follows:

$$SL = k \int_{s1}^{s2} |\Delta \rho / \Delta s|$$

Where k is a constant, ρ is pavement density and s is distance across a surface. In other words, SL is equal to a constant times the average between distance s1 and s2 of the absolute value of a change in density per change in distance. The equation above is accomplished by moving the material analyzing apparatus 1, as embodied by the invention. The movement would be in at least one of a rotation or in straight line. In this methodology, the acquired signal would be a density level plus density variation (DC+AC) as the unit moves.

First, the signal would be AC coupled to provide only a density variation, then this signal would be full-wave rectified and filtered to produce a DC level, which is proportional to density variation. This processing, which can be analog, will produce a signal that is proportional to segregation. This number can displayed for the user by the material analyzing apparatus 1.

The material analyzing apparatus 1, as embodied by the invention, can further calculate a segregation level by rapidly measuring small variations in spatial density across a pavement surface. Signals can be reported to an operator in real time or near-real time values.

Figure 6:
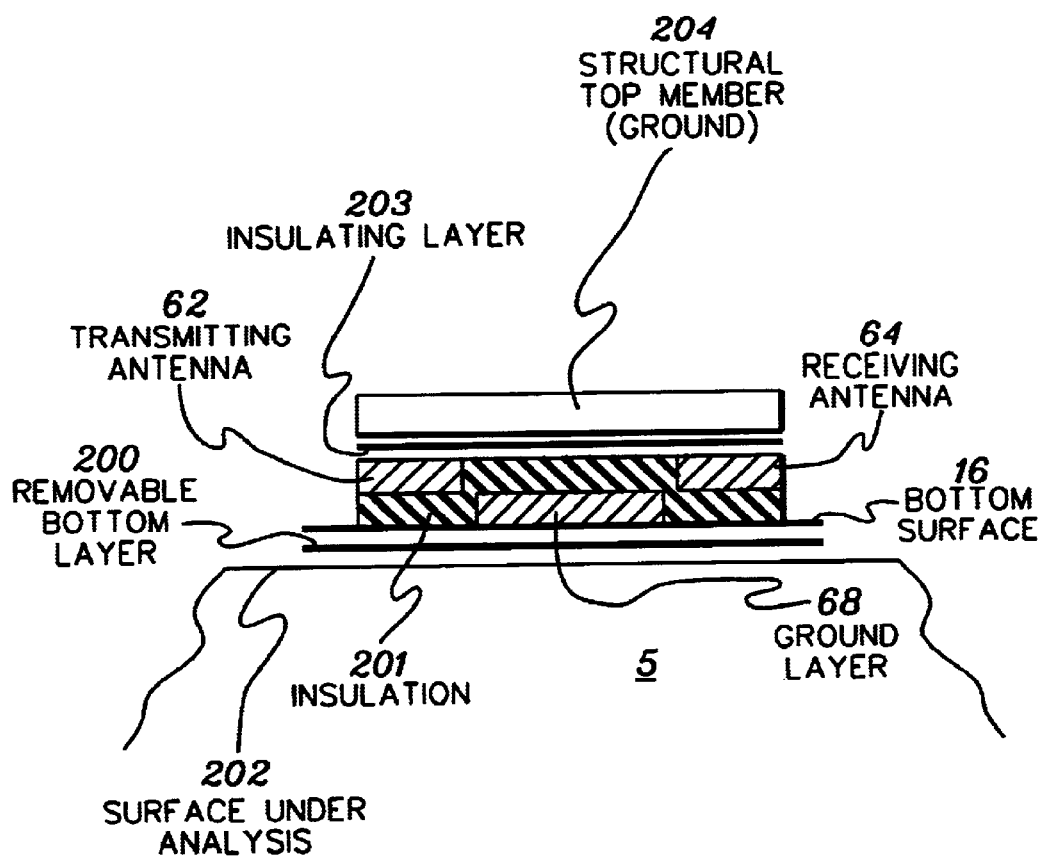
FIG. 6 is a schematic illustration of the antenna for a material characteristics analyzing apparatus, as embodied by the invention.

FIG. 6 is a schematic illustration of the antenna for a material characteristics analyzing apparatus, as embodied by the invention. FIG. 6 comprises the 3—3 cross-sectional cut denoted in FIG. 2. FIG. 6 also shows the bottom surface 16 of the analyzer body 10 (see FIG. 1). FIG. 6 additionally shows a removable bottom member 200 which resides between the bottom surface 16 and the surface under analysis 202. A ground layer 68 with structural insulation 201 on either side thereof forms a layer 71. The next layer 72 above layer 71 comprises the transmitting antenna 62, insulation 201, and the receiving antenna 64. The next layer above layer 72 is a continuous insulating layer 203. An electrically conductive structural top member 204 is above the continuous Insulting Layer 203 and is also electrically connected to ground. Note that FIG. 6 is shown in part as an exploded view such that the spaces shown between the following layers exist for clarity of presentation but are not present in the apparatus of the present invention: between the pavement 5 and the removable bottom member 200, between the layer 72 and the insulation layer 203, and between the insulation layer 203 and the structural top member 204.

Figure 7:
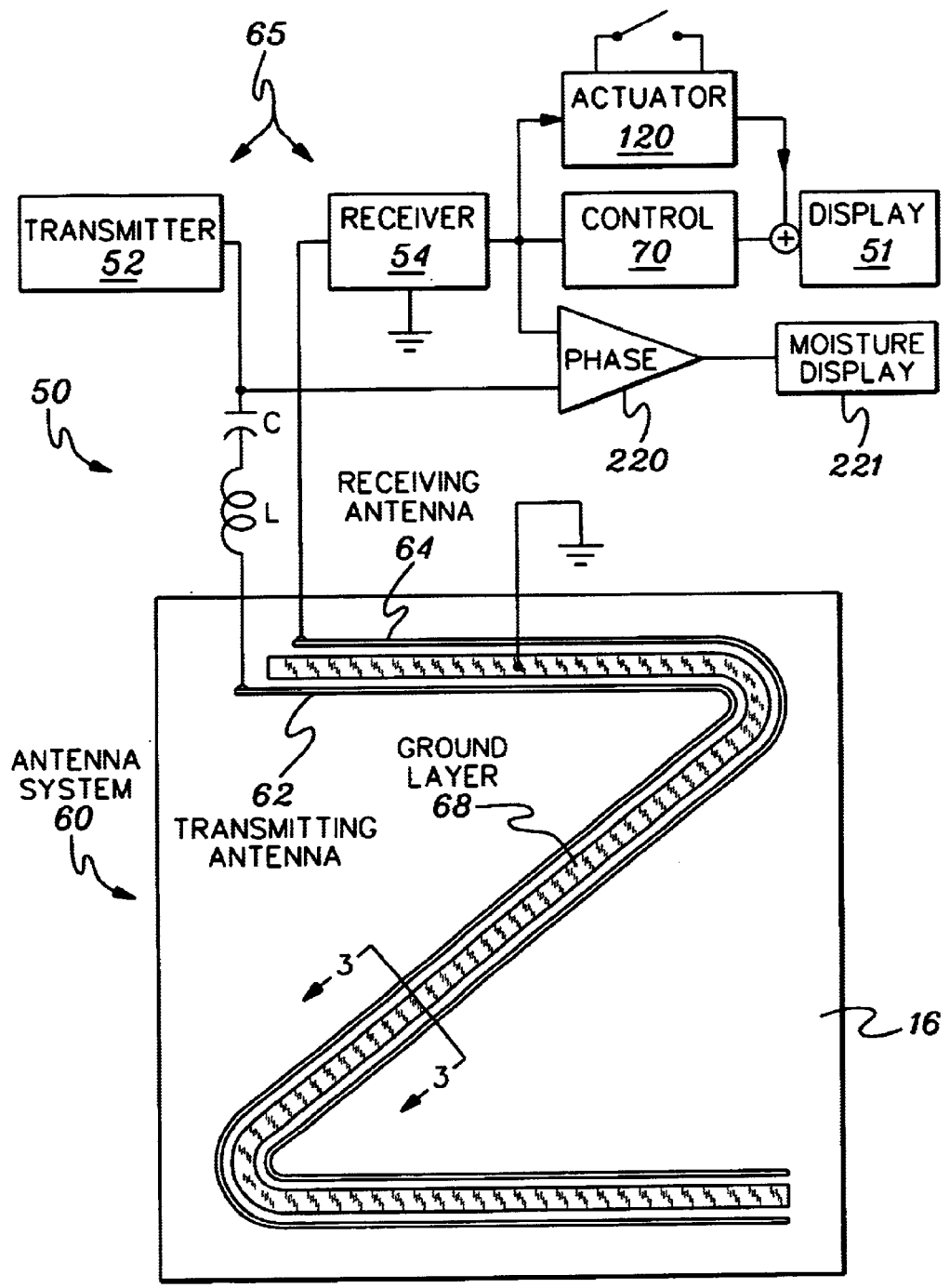
FIG. 7 is a schematic illustration of the circuitry for a moisture content analyzing apparatus, as embodied by the invention.

FIG. 7 is a schematic illustration of the circuitry for a moisture content analyzing apparatus, as embodied by the invention. FIG. 7 is similar to FIG. 2, discussed supra, with the primary exception that FIG. 7 shows a phase block 220 for determining of moisture content and a moisture display 221 for displaying the moisture content so determined. The present invention generally measures material properties of a surface under test. One such material property that is measured is material moisture content. As shown in FIG. 7, the transmitted signal from the transmitting antenna 62 is passed through the material being tested and received by the receiving antenna 64. Moisture present in the material, which may be caused by ambient moisture, will effect the phase relationship between the transmitted and received signals. Dry insulation has a relatively low phase shift (e.g., of the order of 2 degrees). Moist insulation will show a phase shift significantly more than 2 degrees and upward to 20 degrees for high moisture. Thus the phase of the received signal is sensed and calculated by comparing a reference signal from the transmitter 52 to the measured received signal from the receiver 54 and the resultant phase difference is converted to a relative moisture content. The phase difference is determined by the phase block 220 and the moisture content of the material being tested is calculated from the determined phase shift. The calculated moisture content may be displayed on the moisture display 221. The detection of moisture using the present invention may comprise detection of moisture in insulating material (e.g., in electrical insulation on generator stator bars) or in other material (insulating or non-insulating) such as roofing material or thermal insulation.

The signal transmitted by the transmitting antenna 62 in FIG. 7, as well as in all other FIGS. 1–3 and 6, is generally an electromagnetic wave signal such as, inter alia, a VHF signal (e.g., about 50 MHz), a signal in a frequency range of 1 kHz to 50 MHz, etc.

While the embodiments have been described herein, it will be appreciated from the specification that various combinations of elements, variations or improvements therein may be made by those skilled in the art that are within the scope of the invention.

What is claimed is:

1. A material analyzing apparatus, comprising an analyzer body, the analyzer body including:
   a material casing;
   material analyzing circuitry, the material analyzing circuit comprising a transmitter, a receiver, and a control, the material analyzing circuitry being encased by the material casing;
   an antenna system, the antenna system comprising a transmitting antenna, a receiving antenna, and a ground layer; and a coupling structure that couples the antenna system to the material analyzing circuitry, wherein the transmitter of the material analyzing circuitry is adapted to generate an electromagnetic wave signal, the electromagnetic wave signal being adapted to be sent by the transmitting antenna into a material to be analyzed, the receiving antenna receiving a returned signal from the material, the returned signal then adapted to be sent to the receiver and to the control, the control adapted to analyze the returned signal for material characteristics of the material, wherein the transmitting antenna and the receiving antenna of the antenna system and the ground layer comprise a configuration of a two conductor transmission line with in-between ground layer, wherein the antenna system provides a uniform coverage of the electromagnetic wave signal on a surface of the material, wherein the antenna system does not present a dead zone, and wherein the antenna system provides field shaping that results in the returned signal being less effected affected by material surface properties, characteristics, and configurations of a material surface of the material than without said field shaping.

2. The material analyzing apparatus of claim 1, wherein the material characteristics comprise at least one of density, segregation, and moisture content.

3. The material analyzing apparatus of claim 1, wherein the transmitting antenna and the receiving antenna of the antenna system and the ground layer comprise a configuration of a "Z".

4. The material analyzing apparatus of claim 1, wherein the transmitting antenna and receiving antenna are adapted to being located at a greater distance from the material than the ground layer, and wherein the field shaping is due to the transmitting antenna and receiving antenna being located at the greater distance than the distance from the material to the ground layer.

5. The material analyzing apparatus of claim 1, wherein the material characteristics comprise segregation.

6. A material analyzing apparatus for measuring density of a material, the apparatus comprising:

an analyzer body, the analyzer body comprising a material casing;

material analyzing circuitry, the material analyzing circuitry comprising a transmitter, a receiver, and a control, the material analyzing circuitry being encased by the material casing;

an antenna system, the antenna system comprising a transmitting antenna, a receiving antenna, and a ground layer;

a coupling structure that couples the antenna system to the material analyzing circuitry;

wherein the transmitter of the material analyzing circuitry generates an electromagnetic wave signal, the electromagnetic wave signal being adapted to be sent by the transmitting antenna into a material to be analyzed, the receiving antenna receiving a returned signal from the material, the returned signal then sent to the receiver and to the control, the control then able to analyze the returned signal for material characteristics of the material, the density of the material being linearly related to a returned signal, and the control is adapted to determine a density D being generally equal to a measured returned voltage V on the antenna times a constant slope m, plus an offset b, in accordance with:

$$D = m \times V + b, \text{ and}$$

wherein the transmitting antenna and the receiving antenna of the antenna system and the ground layer comprise a configuration of a two conductor transmission line with in-between ground layer, wherein the antenna system provides a uniform coverage of the electromagnetic wave signal on a surface of the material, wherein the antenna system does not present a dead zone, and wherein the antenna system provides field shaping that results in the returned signal being less affected by material surface properties, characteristics, and configurations of a material surface of the material than without said field shaping.

7. The material analyzing apparatus of claim 6, wherein the transmitting antenna and the receiving antenna of the antenna system and the ground layer comprise a configuration of a "Z".

8. The material analyzing apparatus of claim 6, wherein the transmitting antenna and receiving antenna are adapted to being located at a greater distance from the material than the ground layer, and wherein the field shaping is due to the transmitting antenna and receiving antenna being located at the greater distance than the distance from the material to the ground layer.

9. The material analyzing apparatus of claim 6, wherein the material characteristics comprise at least one of density, segregation, and moisture content.

10. The material analyzing apparatus of claim 6, wherein the material characteristics comprise segregation.

11. A method for analyzing a material, the method comprising:

providing an analyzer body, the analyzer body comprising a material casing at exterior surfaces of the analyzer body;

providing material analyzing circuitry, the material analyzing circuitry comprising a transmitter, a receiver, and a control, the material analyzing circuitry being encased by the material casing;

providing an antenna system, the antenna system comprising a transmitting antenna, a receiving antenna, and a ground layer;

coupling the antenna system to the material analyzing circuitry;

generating an electromagnetic wave signal;

transmitting the electromagnetic wave signal by the transmitting antenna;

directing the electromagnetic wave signal into the material;

receiving a returned signal from the material;

sending the returned signal to the receiver and control; and analyzing by the control, the returned signal for material characteristics of the material, wherein the transmitting antenna and the receiving antenna of the antenna system and the ground layer comprise a configuration of a two conductor transmission line with in-between ground layer, and wherein the antenna system provides a uniform coverage of the electromagnetic wave signal on a surface of the material, wherein the antenna system does not present a dead zone, and wherein the antenna system provides field shaping that results in the returned signal being less effected affected by material surface properties, characteristics, and configurations of a material surface of the material than without said field shaping.

12. The method of claim 11, wherein the transmitting antenna and the receiving antenna of the antenna system and the ground layer comprise a configuration of a "Z".

13. The method of claim 11, wherein the material characteristics of the material include moisture content of the material.

14. The method of claim 13, wherein analyzing the returned signal comprises measuring a phase shift caused by the moisture content of the material.

15. The method of claim 11, wherein the transmitting antenna and receiving antenna are adapted to being located at a greater distance from the material than the ground layer, and wherein the field shaping is due to the transmitting antenna and receiving antenna being located at the greater distance than the distance from the material to the ground layer.

16. A method for analyzing a material for measuring density of a material, the method comprising:

providing an analyzer body, the analyzer body comprising a material casing at exterior surfaces of the analyzer body;

providing material analyzing circuitry, the material analyzing circuitry comprising a transmitter, a receiver, and a control, the material analyzing circuit being encased by the material casing;

providing an antenna system, the antenna system comprising a transmitting antenna, a receiving antenna, and a ground layer;

coupling the antenna system to the material analyzing circuitry; and generating an electromagnetic wave signal;

transmitting the electromagnetic wave signal by the transmitting antenna;

directing the electromagnetic wave signal into the material;

receiving any returned signal from the material;

sending the returned signal to the receiver and control; and analyzing, by the control, the returned signal for material density characteristics of the material;

the density of the material being linearly related to a returned signal, and determining density D being generally equal to a measured returned voltage V times a constant slope m, plus an offset b, in accordance with:

$$D = m \times V + b,$$

wherein the transmitting antenna and the receiving antenna of the antenna system and the ground layer comprise a configuration of a two conductor transmission line with in-between ground layer, and wherein the antenna system provides a uniform coverage of the electromagnetic wave signal on a surface of the material, wherein the antenna system does not present a dead zone, and wherein the antenna system provides field shaping that results in the returned signal being less affected by material surface properties, characteristics, and configurations of a material surface of the material than without said field shaping.

17. The method of claim 16, wherein the transmitting antenna and the receiving antenna of the antenna system and the ground layer comprise a configuration of a "Z".

18. The method of claim 16, wherein the transmitting antenna and receiving antenna are adapted to being located at a greater distance from the material than the ground layer, and wherein the field shaping is due to the transmitting antenna and receiving antenna being located at the greater distance than the distance from the material to the ground layer.

19. The method of claim 16, wherein the material characteristics comprise at least one of density, segregation, and moisture content.

20. The method of claim 16, wherein the material characteristics comprise segregation.

* * * * *

UNITED STATES PATENT AND TRADEMARK OFFICE
CERTIFICATE OF CORRECTION

PATENT NO.    : 6,677,763 B2
DATED         : January 13, 2004
INVENTOR(S)   : Donald J. Geisel It is certified that error appears in the above-identified patent and that said Letters Patent is hereby corrected as shown below:

<u>Column 17,</u>
Line 23, delete the word "effected".

<u>Column 19,</u>
Line 4, delete the word "effected".

Signed and Sealed this

Sixteenth Day of March, 2004

JON W. DUDAS
*Acting Director of the United States Patent and Trademark Office*